US00PP35153P2

(12) United States Plant Patent
Hansen

(10) Patent No.: US PP35,153 P2
(45) Date of Patent: May 2, 2023

(54) ***ECHINACEA* PLANT NAMED 'ONE IN A MELON'**

(50) Latin Name: ***Echinacea* hybrid**
Varietal Denomination: One in a Melon

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,772

(22) Filed: Nov. 16, 2022

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

*Primary Examiner* — Kent L Bell

(57) ABSTRACT

The new and distinct cultivar of *Echinacea* plant named 'One in a Melon' with very large fragrant inflorescences on strong, stiff stems producing single whorls of large, melon-colored, strongly-overlapping, ray florets. The large inflorescence produces ray florets that tend to stay nearly horizontal through maturity. The new plant flowers from mid-summer to late summer, and is suitable as a potted plant, for the landscape, and for cut flower arrangements.

2 Drawing Sheets

Botanical denomination: *Echinacea* hybrid.
Cultivar designation: 'One in a Melon'.

STATEMENT REGARDING PRIOR DISCLOSURES UNDER 37 CFR 1.77(b)(6)

The first non-enabling disclosures of the claimed plant, in the form of a photograph and brief description was on a website operated by Walters Gardens, Inc. on Dec. 1, 2021, followed by a photograph and brief description in the "Walters Gardens 2022-2023 Catalog" on Jun. 8, 2022. The claimed plant was first sold on Jan. 10, 2022, to Milmont Greenhouses and to W.W. Greenhouses by Walters Gardens, Inc., who obtained the plant and all information relating thereto, from the inventor. No plants of *Echinacea* 'One in a Melon' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of Coneflower from the genus *Echinacea* and given the cultivar name 'One in a Melon'. The new plant was the result of a cross by the inventor of an unnamed proprietary hybrid known as 15-17-3 (not patented) as the female parent and an unnamed proprietary hybrid known as 15-32-1 (not patented) as the male parent on Aug. 8, 2016, at a wholesale perennial nursery in Zeeland, Mich. The single seedling selected was evaluated initially in trials in the summer of 2017 at the same nursery and assigned the breeder code of 16-78-1.

*Echinacea* 'One in a Melon' has been asexually propagated at the same nursery by crown division since 2019 and also using careful shoot tip tissue culture procedures and found to reproduce plants that exhibit all the characteristics identical to the original plant in successive generations.

*Echinacea* 'One in a Melon' is distinct from all other Coneflowers known to the inventor. The nearest comparison cultivars are: 'Orange You Awesome' U.S. Plant Pat. No. 32,105, 'Balsomador' U.S. Plant Pat. No. 26,639, 'Balsomold' U.S. Plant Pat. No. 30,115, and 'Balsomenco' U.S. Plant Pat. No. 25,523.

The female parent plant, 15-17-3, has narrower ray florets of a lighter yellow and there was less basal branching. The male parent plant, 15-32-1, has a shorter habit with pinkish ray florets and smaller flowers.

'Balsomador' is smaller in habit, the inflorescences are smaller, and ray florets are smaller with a more reddish-orange overlay and droop more in maturity. 'Balsomold' has a shorter habit with smaller inflorescences with ray ray florets that are longer and broader with abaxial sides more greenish yellow. 'Balsomenco' has a shorter habit with smaller inflorescences that have shorter and narrower ray florets of deeper orange. 'Orange You Awesome' is slightly shorter and has ray florets that are less overlapping of a darker tangerine orange color.

SUMMARY OF THE INVENTION

*Echinacea* 'One in a Melon' has not been evaluated under all possible environmental conditions. The phenotype may vary with variations in the environment including: growing temperature, available sunlight, nutrients, water, etc. without a change in the genotype of the plant. The new plant is distinct from its parents and all other *Echinacea* known to the applicant in the following combined traits:

1. Fragrant inflorescences on strong branched stems;
2. Very large, broad inflorescences with a single whorl of ray florets that tend to stay horizontal in inflorescence maturity;
3. Ray florets of melon coloration with matching cones;

4. Ray florets strongly overlapping;
5. Vigorous growth and excellent habit;
6. Dark-green ovate foliage.

BRIEF DESCRIPTION OF THE DRAWINGS

The photographs of 'One in a Melon' demonstrate the overall appearance of the plant including the unique traits. The drawings of the new plant are of a two-year-old plant grown in a partially-shaded greenhouse in Zeeland, Mich. The colors are as accurate as reasonably possible with color reproductions. Some slight variations of color may occur as a result of lighting quality, intensity, wavelength, direction, or reflection.

DETAILED DESCRIPTION OF THE PLANT

Figure 1:
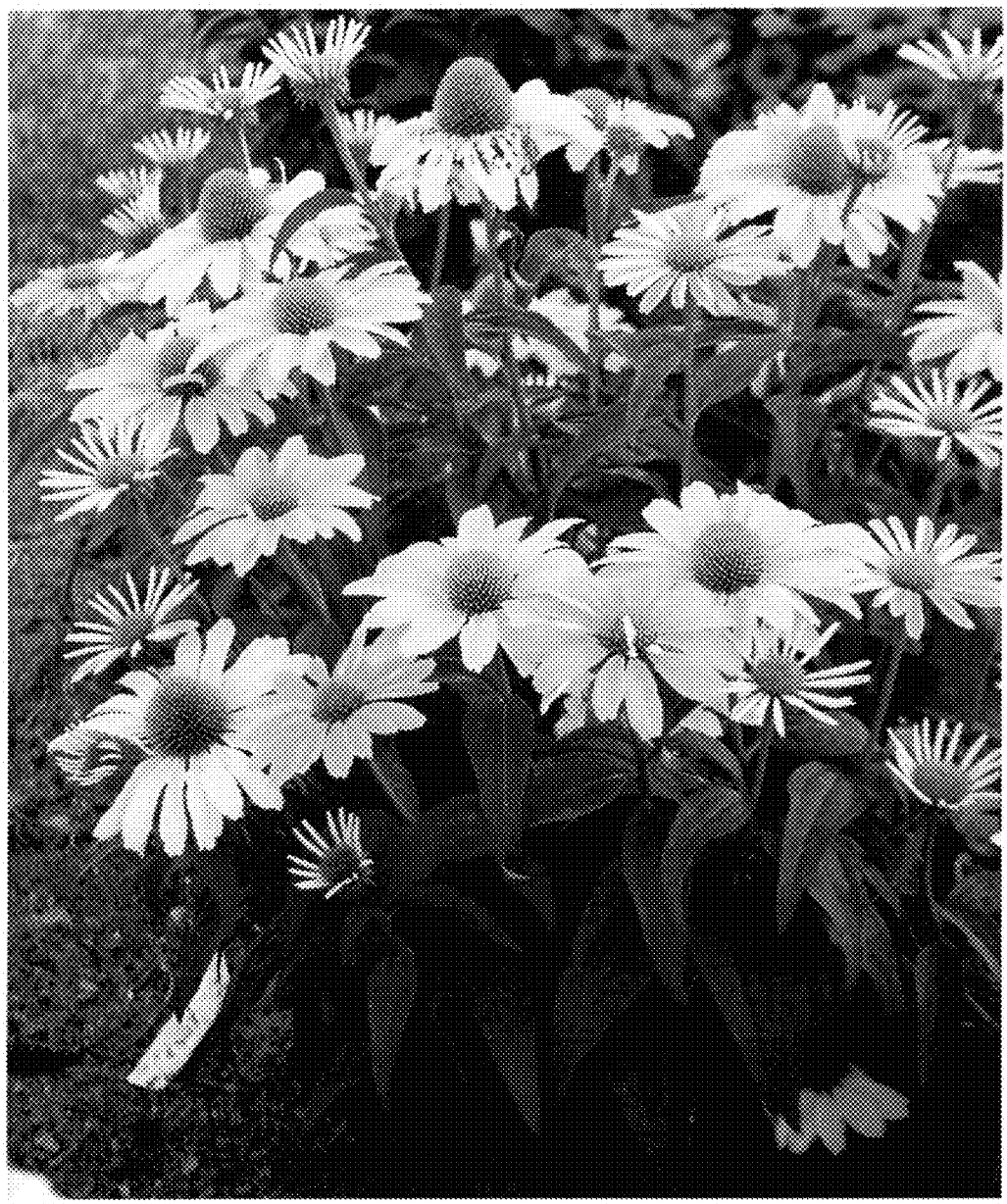
FIG. 1 shows the habit of the new plant in flower.
Figure 2:
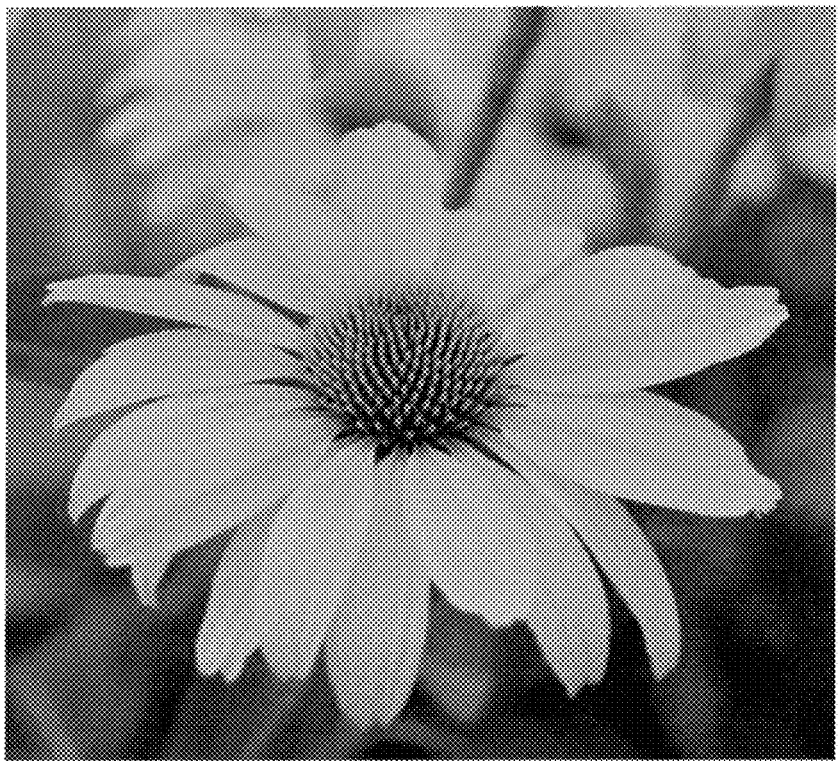
FIG. 2 shows a close-up of an inflorescence from above.

The following description of *Echinacea* 'One in a Melon' is based on observations of two-year-old specimens grown in a partially-shaded greenhouse and in a full-sun trial garden in Zeeland, Mich. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female or seed parent is the proprietary unreleased hybrid 15-17-3 comprising a complex cross with 'Julia' U.S. Plant Pat. No. 24,629 and 'Cleopatra' U.S. Plant Pat. No. 24,631 and male parent is the proprietary unreleased hybrid 15-32-1 comprising a complex crossing with 'Julia' and 'Butterfly Kisses' U.S. Plant Pat. No. 24,458;

Plant habit: Multi-stemmed, freely-branched, hardy herbaceous perennial, flowering to about 73 cm tall and 60 cm wide with foliage to 60 cm tall and 60 cm wide;

Growth rate: Vigorous, finishing in 4-liter containers in about 2 months during the summer;

Roots: Cream-colored, finely branched;

Foliage: Alternate; ovate; acute apex; attenuate base; margin micro-ciliolate and dentate with very small teeth about 0.5 mm long; hirsutulous abaxial and adaxial; to about 19 cm long and 10 cm wide decreasing distally, average about 13 cm long and 5.8 cm wide;

Leaf color: Young leaves adaxial between RHS146A and RHS 137C, abaxial between RHS 146C and RHS 137C; mature leaves adaxial between NN137A and RHS NN137B, abaxial between RHS NN137C and RHS 146A; variegation absent;

Foliage fragrance: Lightly herbal;

Venation: Pinnate; with two major arcuate veins on both sides of the midrib; abaxial midrib and veins costate; glabrous adaxial, hirsutulous abaxial;

Vein color: Adaxial midrib and primary veins nearest RHS 193A, secondary nearest RHS NN137A; abaxial primary veins between RHS 146D and RHS N144A, secondary nearest RHS 137A;

Petiole: Concavo-convex, glabrous adaxial and finely hirsutulous abaxial; to about 10 cm long and 5 mm wide at the base on lowest leaves and decreasing to nearly sessile distally;

Petiole color: Adaxial center nearest 145C and margin between RHS 139A and RHS NN137A, abaxial center between RHS 146D and RHS 145C and margin nearest RHS NN137C;

Stem: Hirsutulous; cylindrical; strong and stiff; to about 71 cm long including peduncle and about 8 mm diameter at base; average 60 cm long and 7 mm diameter;

Stem color: Between RHS 146B and RHS 146C;

Peduncle: Hirsutulous; cylindrical; strong; stiff; about 18 cm long above last leaves and 7 mm diameter at base; quantity per plant about six; aspect upwardly;

Peduncle color: Nearest RHS 146C without significant anthocyanins;

Internode: 6 to 11 per stem; average about 5.6 cm long, shorter proximally and longer distally; node color same as surrounding peduncle;

Branches: Cylindrical; hirsutulous; tightly angled to main stem to about 60° above horizontal: about 2 to 4 branches per stem; to about 20 cm long and 4 mm diameter;

Branch color: Nearest RHS 146C without significant anthocyanins;

Inflorescence: Bracteate head, aggregate of achene; with single whorl of distinct ligulate ray florets and disk florets in a pappus; flowering mid-summer to late summer; initial inflorescence largest, to about 17 cm wide and 8.5 cm tall, with cones 4.5 cm across and 4.3 cm tall; to 4 inflorescences per peduncle;

Inflorescence fragrance: Lightly sweet, honey-like;

Flower persistence: Remaining effective in color for 10 to 14 days depending on temperatures, cone drying on plant and effective into winter;

Involucre: With numerous bracts, about 60 per inflorescence in 4 to 5 whorls; arcuate downward toward peduncle;

Involucre bracts: Lanceolate to linear; narrowly acute apex; truncate base; micro-ciliolate margin; adaxial glabrous to micro-puberulent; abaxial strigillose; to about 13 mm long and 5 mm across decreasing distally; color adaxial center nearest RHS 147C, adaxial margin nearest RHS 139A, abaxial center nearest RHS 138B, and abaxial margins nearest RHS 137B;

Inflorescence buds with ray florets vertical and still enrolled: About 45 mm across and 35 mm tall; ray floret color nearest RHS 160D with spines nearest RHS 141C;

Ray florets: Zygomorphic; arrangement in single whorl, frequently moderately imbricate; ligulate, apex emarginated with two or more notches to 3 mm deep; base attenuate; margin entire; adaxial and abaxial surfaces matte; 16 to 19 per inflorescence; opening to horizontal, drooping up to only 15 degrees below horizontal with maturity; flat, twisting absent; astemonous; ray floret to 68 mm long and 23 mm wide near middle, base 2.5 mm wide; average size 60 mm long, 20 mm wide at center tapering to 2 mm wide at base; thickened veins raised adaxial;

Ray floret color: Changing with maturity; when first horizontal young adaxial between RHS 23A and RHS N25D lightening to between RHS 22B to 23B in mid-open period and nearest RHS 2D before dropping, basal 3 to 4 mm remaining constant between RHS 144A and RHS 146D; abaxial beginning nearest RHS 18B when first horizontal, becoming nearest RHS 18D in mid-open period and between RHS 1D and RHS 145B before dropping with base remaining between RHS 144A and RHS 146D;

Disk florets: About 400 to 500 per head; actinomorphic; perfect; synandrous; produced in raised dome, about 4.3 cm across and 4.5 cm tall;

*Disk floret corolla*.—Fused forming tube; about 6 mm long and 1.7 mm wide, fused in tube in basal 5 mm, free in distal 1 mm; individual disk florets about 0.5 mm wide at fusion; acute apex; entire margin; both surfaces slightly lustrous.

*Disk floret corolla tube color*.—Adaxial and abaxial between RHS 145D and RHS N144D.

*Disk floret androecium*.—Five; synandrous.

*Androecium*.—Present on disk florets only.

*Staminal column*.—About 0.7 mm wide and protrudes from corolla tube about 2 mm; five fused stamens; color nearest RHS N200A.

*Anthers*.—Fused, about 3.0 mm long and 0.7 mm diameter; color nearest RHS N200A.

*Filaments*.—Five; attached to column; thin, less than 0.2 mm diameter and 5 mm long; color nearest RHS NN155D.

*Pollen*.—Globose, less 0.1 mm in diameter; color nearest RHS 14A.

*Gynoecium*.—Single; to 11 mm long; present on both ray and disk florets.

*Style*.—About 8 mm long and 0.3 mm diameter; color between RHS N144D and RHS 145A.

*Stigma*.—Bifid; about 1.5 mm long and 0.3 mm diameter; color between RHS N144D and RHS 145A.

*Fruit*.—Achene; pyramidal; about 4 mm long and 3 mm wide; acute base and fringed flattened apex; color variable nearest RHS 199D and between RHS 202A and RHS 202B.

Receptacle spines: With disk florets; acicular; lustrous; to 13 mm long and 2 mm across near middle;

Spine color: With ray florets first horizontal apices nearest RHS 17A, center portion nearest 143A, and bases nearest RHS NN155C; mature flower apices nearest RHS 151D, central portion between RHS 146D and RHS 143A, and base nearest RHS 151D; after ray florets fall apices nearest RHS 174A, midsection nearest RHS 138A with base nearest RHS 145D; after dried base nearest RHS N200A and distal 5.0 mm nearest RHS 202A;

Disease and pest resistance: Resistance and susceptibility beyond that of other hardy Coneflower cultivars has not been observed.

Growth: The plant grows best with plenty of moisture and adequate drainage but is able to tolerate some drought when mature.

Hardiness: At least from USDA zone 4 through 8.

I claim:

1. A new and distinct cultivar of *Echinacea* plant named 'One in a Melon' as herein described and illustrated.

* * * * *